United States Patent [19]

Georgiev et al.

[11] Patent Number: 4,649,222

[45] Date of Patent: Mar. 10, 1987

[54] 2-(SUBSTITUTED AMINO)-2-[2-HYDROXY-2-ALKYL (OR PHENYL)ETHYL]TRICYCLO[3.3.1.1$^{3,7}$]DECANE HYDROHALIDES

[75] Inventors: Vassil S. Georgiev, Rochester; George B. Mullen, Avon; Patricia A. Swift, Rochester, all of N.Y.

[73] Assignee: Pennwalt Corporation, Philadelphia, Pa.

[21] Appl. No.: 821,298

[22] Filed: Jan. 22, 1986

[51] Int. Cl.$^4$ .............................................. C07C 87/47
[52] U.S. Cl. .................................. 564/459; 564/305; 564/457
[58] Field of Search ..................... 564/459, 305, 457; 514/662

[56] References Cited

U.S. PATENT DOCUMENTS 3,532,748  10/1970  Smith .................................. 564/459
3,729,513   3/1973  Berezin ............................... 564/459

FOREIGN PATENT DOCUMENTS 2411640  10/1974  Fed. Rep. of Germany ...... 564/459

Primary Examiner—Anton H. Sutto
Assistant Examiner—John A. Sopp

[57] ABSTRACT 2-(Substituted amino)-2-[2-hydroxy-2-alkyl (or phenyl)ethyl]tricyclo[3.3.1.1$^{3,7}$]decane hydrohalides are described such as 2-(2-hydroxyoctyl)-2-(methylamino)-tricyclo[3.3.1.1$^{3,7}$]decane hydrochloride. The compounds possess anti-inflammatory, analgesic, anticonvulsant and/or anti-hypoxia activity.

10 Claims, No Drawings

2-(SUBSTITUTED AMINO)-2-[2-HYDROXY-2-ALKYL (OR PHENYL)ETHYL]TRICYCLO[3.3.1.1$^{3,7}$]DECANE HYDROHALIDES

BACKGROUND OF THE INVENTION

In a patent application filed concurrently herewith and commonly assigned, the preparation of substituted spiro (isoxazolidine-3,2'-tricyclo[3.3.1.1$^{3,7}$]decane) derivatives (I) is described. 2-Adamantanone is reacted with an N-substituted hydroxylamine to furnish an adamantyl nitrone which is then reacted with a substituted olefin. The nitrone undergoes a 1,3-dipolar cycloaddition reaction to provide the decane derivatives (I). This preparation scheme is illustrated below:

We have now found that 2-(substituted amino)-2-[2-hydroxy-2-alkyl (or phenyl)ethyl]tricyclo[3.3.1.1$^{3,7}$]-decane hydrohalide can be prepared from I by opening the heterocyclic ring. The new compounds possess anti-inflammatory, analgesic, anticonvulsant and/or antihypoxia activity.

BRIEF SUMMARY OF THE INVENTION

According to this invention there is provided a compound having the formula:

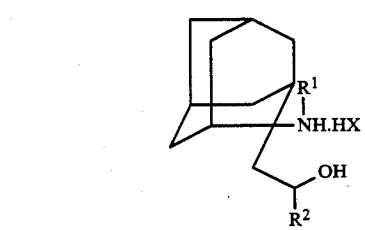

Where R$^1$ is lower alkyl,
Where R$^2$ is branched or unbranched alkyl containing 1 to 18 carbons, phenyl, or phenyl which is mono- or disubstituted with lower alkyl, lower alkoxy, halogen, nitro and combinations thereof, and
Where X is Cl, Br, or I.

DETAILED DESCRIPTION

The heterocyclic ring of the spiro(isoxazolidine-3,2'-tricyclo[3.3.1.1$^{3,7}$]decane) derivatives (I) can be opened to prepare the compounds of the invention by either catalytic hydrogenation of their hydrohalide salts in the presence of a palladium catalyst or by zinc-acetic acid reduction according to the following scheme:

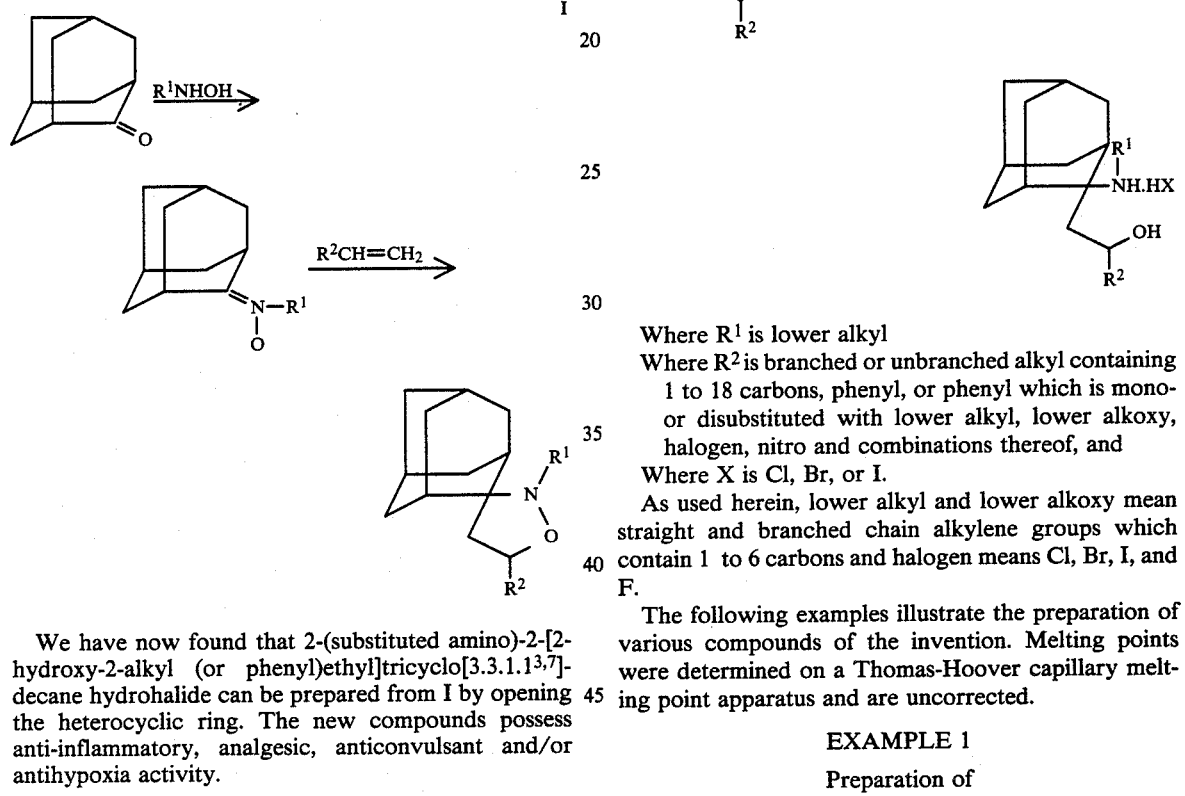

Where R$^1$ is lower alkyl
Where R$^2$ is branched or unbranched alkyl containing 1 to 18 carbons, phenyl, or phenyl which is mono- or disubstituted with lower alkyl, lower alkoxy, halogen, nitro and combinations thereof, and
Where X is Cl, Br, or I.

As used herein, lower alkyl and lower alkoxy mean straight and branched chain alkylene groups which contain 1 to 6 carbons and halogen means Cl, Br, I, and F.

The following examples illustrate the preparation of various compounds of the invention. Melting points were determined on a Thomas-Hoover capillary melting point apparatus and are uncorrected.

EXAMPLE 1

Preparation of 2-(2-Hydroxyoctyl)-2-(methylamino)tricyclo[3.3.1.1$^{3,7}$]decane Hydrochloride (1)

Zinc dust (14 g.) was added portionwise to a solution of 6.56 g. (20 mmol) of the hydrochloride salt of 2-methyl-5-hexylspiro(isoxazolidine-3,2'-tricyclo[3.3.1.1$^{3,7}$]-decane) in 200 ml of 50% by volume aqueous acetic acid. The resulting suspension was heated to 65°–70° C. for 7 hours, then filtered, and the inorganic residue washed with 100 ml of hot water. The combined filtrate was neutralized with 160 g. of sodium bicarbonate and extracted with 500 ml of ether. The organic layer was dried over anhydrous magnesium sulfate and then saturated with hydrogen chloride gas in order to give the hydrochloric salt 1 as a white precipitate. Crystallization of the latter from 50 ml ethyl acetate gave 5.07 g of pure 1 (Mp 182°–185° C.). The compound 1 when tested on rats had antihypoxia and anti-inflammatory (carrageenen-induced rat paw assay) activity.

EXAMPLE 2

The 2-(ethylamino)-2-[2-hydroxy-2-phenylethyl]-tricyclo[3.3.1.1³,⁷]decane hydrochloride (2) (Mp 241°–244° C.) was prepared from 2-ethyl-5-phenyl-spiro(isoxazolidine-3,2'-tricyclo[3.3.1.1.³,⁷]decane) hydrochloride by a procedure similar to that described in Example 1. The compound 2 when tested on rats had anticonvulsant, antihypoxia, analgesic, and anti-inflammatory activity.

EXAMPLE 3

Preparation of 2-(2-Hydroxyoctadecyl)-2-(methylamino)tricyclo[3.3.1.1³,⁷]decane Hydrochloride (3)

5-(Hexadecyl-2-methylspiro(isoxazolidine-3,2'-tricyclo[3.3.1.1³,⁷]decane) hydrochloride (10.0 g, 0.2 mol) was added in one portion to a solution of 1.0 g. of 5% palladium on carbon in 200 ml of acetic acid. The mixture was hydrogenated in a Parr apparatus at room temperature for 72 hours. The reaction mixture was filtered and the filtrate was evaporated under reduced pressure at a temperature of 40° C. The crude, oily residue was dissolved in 250 ml of methylene chloride and washed sequentially with 100 ml of 8 percent by weight aqueous sodium bicarbonate, 100 ml water and 100 ml of brine. The organic extract was dried over anhydrous magnesium sulfate and evaporated to yield a yellow oil which solidified on standing. Subsequent purification by flash chromatography and treatment with ether saturated with hydrogen chloride gas provided 2.76 g of 3 (Mp 145°–149° C.).

Additional compounds of the invention were synthesized in Examples 4 to 9 by procedures similar to that of Example 3.

EXAMPLE 4

2-(2-Hydroxyhexyl)-2-(methylamino)tricyclo[3.3.1.1³,⁷]decane hydrochloride 4 (Mp 181°–185° C.) was prepared from 5-butyl-2-methylspiro(isoxazolidine-3,2'-tricyclo[3.3.1.1³,⁷]decane) hydrochloride.

EXAMPLE 5

2-(2-Hydroxydecyl-2-(methylamino)tricyclo[3.3.1.1³,⁷]decane hydrochloride (5) (Mp 162°–166° C.) was prepared from 2-methyl-5-octylspiro(isoxazolidine-3,2'-tricyclo[3.3.1.1.³,⁷]decane) hydrochloride.

EXAMPLE 6

2-(2-Hydroxyduodecyl)-2-(methylamino)tricyclo[3.3.1.1³,⁷]decane hydrochloride (6) (Mp 156°–158° C.) was prepared from 5-decyl-2-methylspiro(isoxazolidine-3,2'-tricyclo[3.3.1.1.³,⁷]decane) hydrochloride.

EXAMPLE 7

2-(2-Hydroxyhexadecyl)-2-(methylamino)tricyclo[3.3.1.1³,⁷]decane hydrochloride (7) (Mp 148°–152° C.) was prepared from 2-methyl-5-tetradecylspiro(isoxazolidine-3,2'-tricyclo[3.3.1.1.³,⁷]decane) hydrochloride.

EXAMPLE 8

2-(2-Hydroxyeicosyl)-2-(methylamino)tricyclo[3.3.1.1.³,⁷]decane hydrochloride (8) (Mp 141°–145° C.) was prepared from 2-methyl-5-oxtadecylspiro(isoxazolidine-3,2'-tricyclo[3.3.1.1.³,⁷]decane) hydrochloride.

EXAMPLE 9

2-(2-Hydroxy-2-phenyl)ethyl-2-(methylamino)tricyclo[3.3.1.1.³,⁷]decane hydrochloride (9) (Mp >210° C.) was prepared from 2-methyl-5-phenylspiro(isoxazolidine-3,2'-tricyclo[3.3.1.1³,⁷]decane) hydrochloride.

We claim:

1. A compound having the formula:

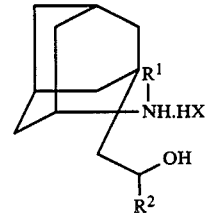

Where $R^1$ is lower alkyl,

Where $R^2$ is branched or unbranched alkyl containing 1 to 18 carbons, phenyl, or phenyl which is mono- or disubstituted with lower alkyl, lower alkoxy, halogen, nitro and combinations thereof, and Where X is Cl, Br, or I.

2. A compound according to claim 1 which is 2-(2-hydroxyoctyl)-2-(methylamino)tricyclo[3.3.1.1³,⁷]decane hydrochloride.

3. A compound according to claim 1 which is 2-(ethylamino)-2-(2-hydroxy-2-phenyl)ethyltricyclo[3.3.1.1³,⁷]decane hydrochloride.

4. A compound according to claim 1 which is 2-(2-hydroxyoctadecyl)-2-(methylamino)tricyclo[3.3.1.1³,⁷]-decane hydrochloride.

5. A compound according to claim 1 which is 2-(2-hydroxyhexyl)-2-(methylamino)tricyclo[3.3.1.1³,⁷]decane hydrochloride.

6. A compound according to claim 1 which is 2-(2-hydroxydecyl)-2-(methylamino)tricyclo[3.3.1.1³,⁷]decane hydrochloride.

7. A compound according to claim 1 which is 2-(2-hydroxyduodecyl)-2-(methylamino)tricyclo[3.3.1.1³,⁷]-decane hydrochloride.

8. A compound according to claim 1 which is 2-(2-hydroxyhexadecyl)-2-(methylamino)tricyclo[3.3.1.1³,⁷]decane hydrochloride.

9. A compound according to claim 1 which is 2-(2-hydroxyeicosyl)-2-(methylamino)tricyclo[3.3.1.1.³,⁷]-decane hydrochloride.

10. A compound according to claim 1 which is 2-(2-hydroxy-2-phenyl)ethyl-2-(methylamino)tricyclo[3.3.1.1.³,⁷]decane hydrochloride.

* * * * *